(12) United States Patent
Dunning et al.

(10) Patent No.: US 12,350,670 B2
(45) Date of Patent: Jul. 8, 2025

(54) DROPLET MANIPULATION DEVICE AND METHOD

(71) Applicant: LIGHTCAST DISCOVERY LTD., Cambridge (GB)

(72) Inventors: Alexander Dunning, Cambridge (GB); Andreas Michael Waeber, Cambridge (GB)

(73) Assignee: LIGHTCAST DISCOVERY LTD., Cambridge (GB)

( * ) Notice: Subject to any disclaimer, the term of this patent is extended or adjusted under 35 U.S.C. 154(b) by 1217 days.

(21) Appl. No.: 17/056,150

(22) PCT Filed: May 17, 2019

(86) PCT No.: PCT/EP2019/062791
§ 371 (c)(1),
(2) Date: Nov. 17, 2020

(87) PCT Pub. No.: WO2019/219905
PCT Pub. Date: Nov. 21, 2019

(65) Prior Publication Data
US 2021/0213453 A1    Jul. 15, 2021

(30) Foreign Application Priority Data
May 18, 2018 (EP) .................................. 18173365

(51) Int. Cl.
*B01L 3/00* (2006.01)

(52) U.S. Cl.
CPC . *B01L 3/502784* (2013.01); *B01L 2300/0645* (2013.01); *B01L 2300/0663* (2013.01); *B01L 2300/0816* (2013.01); *B01L 2400/0424* (2013.01); *B01L 2400/0427* (2013.01)

(58) Field of Classification Search
None
See application file for complete search history.

(56) References Cited

U.S. PATENT DOCUMENTS

| | | | |
|---|---|---|---|
| 6,565,727 B1 | 5/2003 | Shenderov | |
| 2003/0224528 A1 | 12/2003 | Chiou et al. | |
| 2006/0039823 A1 | 2/2006 | Yamakawa et al. | |
| 2008/0169195 A1* | 7/2008 | Jones | G02B 26/005 |
| | | | 204/600 |
| 2013/0217103 A1 | 8/2013 | Bauer | |
| 2013/0233425 A1 | 9/2013 | Srinivasan et al. | |
| 2014/0216559 A1 | 8/2014 | Foley | |
| 2015/0027889 A1 | 1/2015 | Pollack et al. | |
| 2015/0298125 A1 | 10/2015 | Ermakov | |
| 2015/0306598 A1 | 10/2015 | Khandros et al. | |
| 2016/0158748 A1 | 6/2016 | Wu et al. | |
| 2016/0160259 A1 | 6/2016 | Du | |
| 2016/0195492 A1 | 7/2016 | Bauer | |
| 2017/0130265 A1 | 5/2017 | Balmforth et al. | |
| 2018/0057872 A1 | 3/2018 | Balmforth et al. | |
| 2018/0080074 A1 | 3/2018 | Balmforth et al. | |

FOREIGN PATENT DOCUMENTS

| | | | |
|---|---|---|---|
| EP | 1 627 685 | 2/2006 | |
| WO | WO 2005100541 | * 10/2005 | .............. C12M 3/04 |
| WO | WO2010151794 | * 12/2010 | ................ C02F 1/40 |
| WO | 2011/126892 | 10/2011 | |
| WO | 2014/053853 | 4/2014 | |
| WO | 2014/167323 | 10/2014 | |
| WO | 2015/164846 | 10/2015 | |
| WO | 2016/012789 | 1/2016 | |

OTHER PUBLICATIONS

International Search Report issued Jul. 10, 2019 in corresponding PCT Application No. PCT/EP2019/062791.
Written Opinion of the International Searching Authority issued Jul. 10, 2019 in corresponding PCT Application No. PCT/EP2019/062791.
Chiou et al., "Continuous optoelectrowetting for picoliter droplet manipulation", Applied Physics Letter, 2008, vol. 93, pp. 221110-1-22110-3.
Pei, Shao Ning, "Optofluidic Devices for Droplet and Cell Manipulation", University of California at Berkeley, 2015, USB/EECS-2015-119, 108 total pages.
European Patent Application No. 17180391.9 filed Jul. 7, 2017, 28 pages.
European Patent Application No. 17177204.9 filed Jun. 21, 2017, 18 pages.
European Patent Application No. 16187112.4 filed Sep. 2, 2016, 24 pages.
European Patent Application No. 16187493.8 filed Sep. 6, 2016, 28 pages.
European Patent Application No. 16189791.3 filed Sep. 10, 2016, 27 pages.
European Patent Application No. 17171168.2 filed May 15, 2017, 27 pages.

* cited by examiner

Primary Examiner — Ann Montgomery
(74) Attorney, Agent, or Firm — Porter Wright Morris & Arthur LLP

(57) ABSTRACT

A microfluidic device for manipulating microdroplets is provided. It includes (a) a microfluidic space defined at least in part by juxtaposition of opposed containing walls and (b) disposed on or within at least one of the containing walls optoelectrowetting electrode locations arranged in a pathway characterised in that in at least one direction substantially parallel to that of the pathway a region of the microfluidic space continuously varies or may be caused to continuously vary in depth; for example by tapering or cantilevering a resilient part of one of the walls. The device and its associated method of use are suitable components for nucleic acid sequencers and biomedical analytical devices.

7 Claims, No Drawings

DROPLET MANIPULATION DEVICE AND METHOD

This invention relates to a device and associated method for manipulating microdroplets using optoelectrowetting forces. It is especially useful for systematically manipulating large numbers of microdroplets containing for example nucleotides, polynucleotides or cells which, for example, might be encountered in nucleic acid sequencers or biomedical analytical devices such as devices used for immunoassays.

Devices for manipulating droplets or magnetic beads have been previously described in the art; see for example U.S. Pat. No. 6,565,727, US20130233425 and US20150027889. In the case of droplets, this may be typically achieved by causing the droplets, for example in the presence of an immiscible carrier fluid, to travel through a microfluidic space defined by two opposed walls of a cartridge or microfluidic tubing. Embedded within one or both of these walls are microelectrodes covered with a dielectric layer each of which is connected to an A/C biasing circuit capable of being switched on and off rapidly at intervals to modify the electric field characteristics of the layer. This gives rise to localised directional capillary forces in the vicinity of the microelectrodes which can be used to steer the droplet along one or more predetermined pathways. Such devices, which employ what is hereinafter referred to as 'real' electrodes, are known in the art by the acronym EWOD (Electrowetting on Dielectric).

A variant of this approach, in which the electrowetting forces are optically-mediated, known in the art as optoelectrowetting or OEWOD, has been disclosed in, for example, US20030224528, US20150298125, US20160158748, US20160160259 and Applied Physics Letters 93 221110 (2008). In particular, the first of these three patent applications discloses various microfluidic devices which include a microfluidic cavity defined by first and second walls and wherein the first wall is of composite design and comprised of substrate, photoconductive and insulating (dielectric) layers. In this single-sided embodiment, between the photoconductive and insulating layers is disposed an array of conductive cells which are electrically isolated from one another and coupled to the photoactive layer and whose functions are to generate corresponding optoelectrowetting electrode locations on the insulating layer. At these locations, the surface tension properties of the droplets can be modified by means of an electrowetting field as described above. The conductive cells may then be temporarily switched on by light impinging on the photoconductive layer. This approach has the advantage that switching is made much easier and quicker although its utility is to some extent still limited by the arrangement of the electrodes. Furthermore, there is a limitation as to the speed at which droplets can be moved and the extent to which the actual droplet pathway can be varied.

Double-sided embodiments of this latter approach has been disclosed in University of California at Berkeley thesis UCB/EECS-2015-119 by Pei. In one example, a cell is described which allows the manipulation of relatively large droplets in the size range 100-500 µm using optoelectrowetting across a surface of Teflon AF deposited over a dielectric layer using a light-pattern over electrically-biased amorphous silicon. However, in the devices exemplified the dielectric layer is thin (100 nm) and only disposed on the wall bearing the photoactive layer.

US20080169195 describes a conventional EWOD device with tapering electrowetting pathways. This is achieved by varying the thickness of the dielectric layer and having the underlying substrates remain parallel. By this means, (a) the capacitative response of the different regions varies in a non-continuous way so that the droplets can be switched in and out of the regions by tuning the input frequency and (b) the device transitions between dielectrophoresis and EWOD forces during the situation. Because of this geometry, the device is bistable in operation whereas that described below is monostable.

WO2011126892 also describes a device based on conventional EWOD. However, here the changes in the distance between the containing walls varies stepwise as opposed to a continuous tapering way.

Recently in our pending application EP17177204.9 we have described a device for manipulating microdroplets which uses optoelectrowetting to provide the motive force. In this OEWOD device, the microdroplets are translocated through a microfluidic space defined by containing walls; for example, a pair of parallel plates having the microfluidic space sandwiched therebetween. At least one of the containing walls includes what are hereinafter referred to as 'virtual' optoelectrowetting electrodes locations which are generated by selectively illuminating an area of a semiconductor layer buried within. By selective illumination of the layer with light from a separate light source, a virtual pathway of electrowetting electrode locations can be generated transiently along which the microdroplets can be caused to move. In our corresponding application EP17180391.9, use of this device as an operative part of a nucleic acid sequencer is described.

We have now developed an improved version of our device suitable for use with the electrodes of the OEWOD type. In this development, the containing walls defining the microfluidic space and therefore the electrodes associated therewith are arranged so that the microfluidic space tapers towards an apex where the minor dimension of the space, hereinafter referred to as the depth of the space, reduces to a minimum and in certain embodiments reaches or approaches zero. Suitably this tapering is arranged in a direction substantially parallel to at least some of the microdroplet pathways defined by the electrode locations. This directional tapering of the depth of the microfluidic space has the advantage that microdroplets translocating along the pathway are exposed to conditions where they progressively expand or are compressed depending on their direction of travel.

This ability to manipulate the morphology of the microdroplets within a device has a number of advantages. For example, where the microfluidic space is deep relative to the diameters of the microdroplets in their natural, spherical shape, the microdroplets move relatively fast because their surface interaction with each electrode location is at a minimum. For some applications or in some areas of a device such as a nucleic acid sequencer or device performing immunoassays this is desirable as it enables microdroplets to be processed quickly. It has also been found that, under such conditions, chemical reactions occurring within the microdroplets proceed quicker and detection of the microdroplets contents by optical means exhibits a better signal to noise ratio; an especially important requirement when the concentration of detectable material is very low. On the other hand, where the depth is relatively shallow and the microdroplets undergo significant compression/flattening they are easier to split into sub-droplets or to merge with secondary microdroplets as a means of introducing additional reactants thereinto. From this, it is clear that for many applications and devices there is a need for a device where microdroplets can be subjected to different regimes requiring different degrees of compression in relatively proximate spaces.

According to the present invention, there is provided a microfluidic device for manipulating microdroplets including (a) a microfluidic space defined at least in part by an arrangement of opposed containing walls and (b) disposed on or within at least one of the containing walls optoelectrowetting locations arranged in a pathway characterised in that in at least one direction substantially parallel to that of the pathway a region of the microfluidic space continuously varies or may be caused to continuously vary in depth.

The microfluidic space defined by the containing walls can in principle take any form as long as it includes a region which continuously varies in depth in a non-stepwise way in at least one direction substantially parallel to that of at least one of the pathways. In one embodiment, this variation may be caused by continuous variation of the distance between the two containing walls which in turn have dielectric overlayers of constant thickness. In another embodiment the variation can be achieved by varying the thickness of this layer whilst maintaining the walls themselves a constant distance apart. In yet another the containing walls may themselves may continuously vary in thickness in the region concerned.

In one embodiment, the region progressively tapers up or down in depth in at least one direction substantially parallel to that of a microfluidic pathway. By the term 'substantially parallel' as used herein is meant either exactly parallel or at small angle to the parallel; for example, at an angle of less than 15, 10 or 5 degrees thereto. For example, as described above, the microfluidic space may comprise a thin layer sandwiched between two plate-like structures with depth of the layer tapering towards a minimum such that the microfluidic space is wedge-shaped. In another, either or both of the containing walls may be resilient or include an area of resilient material so that the depth of the microfluidic space by caused to vary either permanently or temporarily by deforming it using an applied force; for example by the action of a mechanical probe providing a cantilevering force or by the application of hydrostatic pressure to a thinned down section of the wall(s).

In one embodiment, the microfluidic space is a microfluidic channel or pipe with the tapering occurring along its major axis so that the channel or pipe takes a conical or frustoconical morphology. In another, tapering is such as to create a microfluidic space wherein the distance between the two containing walls narrows downwards to or upwards from a maximum dimension of 150% of the microdroplets' diameters in an uncompressed state. Preferably, the maximum dimension should be less than 100 microns. In yet another embodiment, the microfluidic space tapers down to less than or equal to the diameter of a particle positioned at a particle-receiving location located at or close to the apex; for example, to a value in the range from 0.001 to 10 microns.

If tapering of the microfluidic space is to be achieved by a corresponding orientation of one or both of the internal surfaces of the containing walls, it is convenient to do so by including one or more spacers such as beads, pillars, ridges and the like made out of for example a dielectric material. In one embodiment, these spacers may be created using an intermediate resist layer which has been produced on one or both of the containing walls by photo-patterning.

Adjacent the microfluidic space and disposed on or within at least one of the containing walls of the device are a plurality of optoelectrowetting electrodes locations arranged so as to generate one or more virtual pathways along which the microdroplets can be driven by propulsive dielectrophoretic or electrowetting forces. In one embodiment, these electrode locations are generated by light falling on regions of a photoactive layer (e.g. a semiconductor layer) disposed on or within the containing wall beneath a dielectric layer. In an embodiment of this approach, the other containing wall likewise acts as a ground electrode when a voltage is applied across the two. One preferred embodiment of such optoelectrowetting or OEWOD configurations which has been described in our earlier application referred to above employs composite containing walls and is characterised by the following components:

a first composite wall comprised of:
 a first substrate
 a first conductor layer on the substrate having a thickness in the range 70 to 250 nm;
 a photoactive layer activated by electromagnetic radiation in the wavelength range 400-1000 nm on the conductor layer having a thickness in the range 300-1500 nm and
 a first dielectric layer on the photoactive layer having a thickness in the range 30 to 160 nm;
a second composite wall comprised of:
 a second substrate;
 a second conductor layer on the substrate having a thickness in the range 70 to 250 nm and
 optionally a second dielectric layer on the conductor layer having a thickness in the range 30 to 160 nm
 wherein the exposed surfaces of the first and second dielectric layers are disposed less than 180 μm apart to define a microfluidic space adapted to contain microdroplets;
an A/C source to provide a voltage across the first and second composite walls connecting the first and second conductor layers;
at least one source of electromagnetic radiation having an energy higher than the bandgap of the photoexcitable layer adapted to impinge on the photoactive layer to induce corresponding virtual optoelectrowetting electrode locations on the surface of the first dielectric layer and
means for manipulating the points of impingement of the electromagnetic radiation on the photoactive layer so as to vary the disposition of the virtual optoelectrowetting electrode locations thereby creating at least one electrowetting pathway along which the microdroplets may be caused to move.

In another embodiment, this OEWOD configuration is characterised by the following components:

a first composite wall comprised of:
 a first transparent substrate
 a first transparent conductor layer on the substrate having a thickness in the range 70 to 250 nm;
 a photoactive layer activated by electromagnetic radiation in the wavelength range 400-1000 nm on the conductor layer having a thickness in the range 300-1000 nm and
 a first dielectric layer on the conductor layer having a thickness in the range 120 to 160 nm;
a second composite wall comprised of:
 a second substrate;
 a second conductor layer on the substrate having a thickness in the range 70 to 250 nm and
 optionally a second dielectric layer on the conductor layer having a thickness in the range 25 to 50 nm wherein the exposed surfaces of the first and second dielectric layers are disposed less than 10 µm apart to define a microfluidic space adapted to contain microdroplets;

an A/C source to provide a voltage across the first and second composite walls connecting the first and second conductor layers;

at least one source of electromagnetic radiation having an energy higher than the bandgap of the photoexcitable layer adapted to impinge on the photoactive layer to induce corresponding virtual optoelectrowetting electrode locations on the surface of the first dielectric layer and means for manipulating the points of impingement of the electromagnetic radiation on the photoactive layer so as to vary the disposition of the virtual optoelectrowetting electrode locations thereby creating at least one electrowetting pathway along which the microdroplets may be caused to move.

In another embodiment of these particular OEWOD configurations, the first and second composite walls form or are integral with the containing walls of a transparent chip or cartridge with the tapering microfluidic space sandwiched between. In another, the first substrate and first conductor layer are transparent enabling light from the source of electromagnetic radiation (for example multiple laser beams or LED diodes) to impinge on the photoactive layer. In another, the second substrate, second conductor layer and second dielectric layer are transparent so that the same objective can be obtained. In yet another embodiment, all these layers are transparent.

Suitably, the first and second substrates are made of a material which is mechanically strong; for example, glass, silicon, metal or an engineering plastic. In one embodiment, the substrates may have a degree of flexibility. In yet another embodiment, the first and second substrates have a thickness in the range 100-1000 µm.

The first and second conductor layers are suitably located on one surface of the first and second substrates and typically have a thickness in the range 70 to 250 nm, preferably 70 to 150 nm. In one embodiment, at least one of these layers is made of a transparent conductive material such as Indium Tin Oxide (ITO), a very thin film of conductive metal such as silver or a conducting polymer such as PEDOT or the like. These layers may be formed as a continuous sheet or a series of discrete structures such as wires. Alternatively, the conductor layer may be a mesh of conductive material with the electromagnetic radiation being directed between the interstices of the mesh.

The photoactive layer is suitably comprised of a semiconductor material which can generate localised areas of charge in response to stimulation by the source of electromagnetic radiation. Examples include hydrogenated amorphous silicon layers having a thickness in the range 300 to 1000 nm. In one embodiment, the photoactive layer is activated by the use of visible light.

The photoactive layer, in the case of the first composite wall and optionally the conducting layer in the case of the second composite wall, is coated with a dielectric layer which is typically in the thickness range from 120 to 160 nm. The dielectric properties of this layer preferably include a high dielectric strength of $>10^7$ V/m and a dielectric constant of $>3$. Preferably, it is as thin as possible consistent with avoiding dielectric breakdown. In one embodiment, the dielectric layer is selected from high purity alumina or silica, hafnia or a thin non-conducting polymer film.

In another embodiment of this OEWOD configuration, at least the first dielectric layer, preferably both, are coated with an anti-fouling layer to assist in the establishing the desired microdroplet/carrier medium/surface contact angle at the various virtual optoelectrowetting electrode locations, and additionally to prevent the contents of the microdroplets adhering to the surface and being diminished as they translocate across the device. If the second containing wall does not comprise a second dielectric layer, then the second anti-fouling layer may be applied directly onto the second conductor layer. For optimum performance, the anti-fouling layer should assist in establishing a microdroplet/carrier medium/surface contact angle in the range 50-110° when measured as an air-liquid-surface three-point interface at 25° C. Depending on the choice of carrier phase, the same contact angle of microdroplets in a device filled with an aqueous emulsion will be higher; for example greater than 100°. In one embodiment, these layer(s) have a thickness of less than 50 nm and are typically monomolecular. In another, these layers are comprised of a polymer of an acrylate ester such as methyl methacrylate or a derivative thereof substituted with hydrophilic groups; e.g. alkoxysilyl. Preferably either or both of the anti-fouling layers are hydrophobic to ensure optimum performance. In another embodiment, these layer(s) are comprised of monomolecular layers which have been functionalised with suitable end-groups, e.g. perfluoro moieties.

In this OEWOD configuration, the first and second containing walls are biased using a source of A/C power attached to the conductor layers to provide a voltage potential difference therebetween.

Irrespective of the particular OEWOD arrangement adopted, the device further optionally includes a source of electromagnetic radiation having a wavelength in the range 400-1000 nm and an associated energy higher than the bandgap of the photoexcitable layer. Suitably, the photoactive layer will be activated at the virtual optoelectrowetting electrode locations where the incident intensity of the radiation employed is in the range 0.001 to 0.2 $Wcm^{-2}$. The source of electromagnetic radiation is, in one embodiment (such as the OEWOD configuration described above) modulated and in another spatially digitized (e.g. pixelated) so as to produce corresponding photoexcited regions on the photoactive layer which are likewise spatially digitized. By this means, corresponding spatially digitized virtual optoelectrowetting electrode locations are created on the internal surface of the containing wall. This makes the device very flexible and the corresponding virtual electrowetting pathways highly programmable.

The OEWOD configuration taught above is particularly advantageous in that the resulting composite stack has the anti-fouling and contact-angle modifying properties from the coated monolayer (or very thin functionalised layer) combined with the performance of a similar or thicker intermediate layer having high-dielectric strength and high-dielectric constant (such as aluminium oxide or hafnia). The resulting layered structure is highly suitable for the manipulation of very small volume microdroplets; such as those having diameters less than 10 µm, for example in the range 2 to 8, 2 to 6 or 2 to 4 µm in their uncompressed state. For these microdroplets, the performance advantage of having the total non-conducting stack above the photoactive layer is extremely useful as the droplet dimensions start to approach the thickness of the dielectric stack and hence the field gradient across the droplet (a requirement for electrowetting-induced motion) is reduced for the thicker dielectric.

The layered structure taught above is also suitable for the manipulation of microdroplets whose diameters range from 10 to 100 µm.

Where the source of electromagnetic radiation is spatially digitized, it is suitably supplied either directly or indirectly using an optionally reflective screen illuminated by light from LEDs or LCDs. Alternatively, these light sources may be coupled to the photoactive layer using lenses. This enables highly complex patterns of virtual optoelectrowetting electrode locations to be rapidly created and destroyed in the first dielectric layer thereby enabling the microdroplets to be precisely steered along arbitrary virtual pathways using closely-controlled electrowetting forces. This is especially advantageous when the aim is to manipulate many thousands of such microdroplets simultaneously along multiple electrowetting pathways. Such electrowetting pathways can be viewed as being constructed from a continuum of virtual optoelectrowetting electrode locations on the first dielectric layer.

The points of impingement of the sources of electromagnetic radiation on the photoactive layer can be any convenient shape including the conventional circular. In one embodiment, the morphologies of these points are determined by the morphologies of the corresponding pixelations and in another correspond wholly or partially to the morphologies of the microdroplets once they have entered the microfluidic space. In one preferred embodiment, the points of impingement and hence the optoelectrowetting electrode locations may be crescent-shaped and orientated in the intended direction of travel of the microdroplet. Suitably, these optoelectrowetting electrode locations are smaller than the surface area of the microdroplet surface adhering to the first or second wall.

Irrespective of the OEWOD configuration adopted, the second containing wall may also include a photoactive layer which enables a second set of virtual optoelectrowetting electrode locations to also be induced on the second dielectric layer by means of the same or different source of electromagnetic radiation. The addition of a second dielectric layer enables transition of the wetting edge from the upper to the lower surface of the electrowetting device, and the application of more electrowetting force to each microdroplet.

The device of the invention may generally further comprise at least one inlet in at least one of the containing walls for introducing the microdroplets into the microfluidic space. Such inlets may be patterned with one or more structures (necks, cavities, blades etc.) and virtual optoelectrowetting electrode locations which enable individual microdroplets to be severed from a larger parent droplet at or close to the mouth of the inlet. They may also be open channels for introducing pre-dropletised emulsions and if desired interfaced to other components such as emulsion-containing tubing and pumps.

In another embodiment, the optoelectrowetting electrode locations may be arranged to generate multiple pathways which intersect with each other so that the translocating microdroplets can be caused to merge with secondary microdroplets at one or more points of intersection in the tapered microfluidic space. In this embodiment, the secondary microdroplets may be delivered by one or more secondary pathways running at an angle or even perpendicular to the principal pathways carrying the translocating microdroplets.

In another embodiment the device may include at least one particle-receiving location at or towards the apex of the tapering where a microbead or the like bearing an analyte sample can be located. This embodiment is especially suitable where it is envisaged that the translocating microdroplets will traverse the micro bead for the purpose of effecting a chemical reaction with the analyte located thereon. In yet another embodiment, the device may generally include a transparent window located in one or both of the containing walls so that the microdroplets may be inspected visually or interrogated with light; for example, for the purpose of detecting microdroplet fluorescence, absorption or chemiluminescence. Suitably, this window is located in a region of the tapering microfluidic space. However, it is also possible to dispense with such a window by rendering the walls of the device completely transparent.

Generally, the device of the invention may further include a means to analyse the contents of the microdroplets disposed either within the device itself or at a point downstream thereof. In one embodiment, this analysis means may comprise a second source of electromagnetic radiation arranged to impinge on the microdroplets and a photodetector for detecting fluorescence, absorption or chemiluminescence by chemical components contained within.

Associated with the device of the invention there is a corresponding method for manipulating microdroplets translocating through a microfluidic space defined by opposed containing walls at least one of which comprises a plurality of optoelectrowetting electrode locations characterised in that in at least one direction parallel to the direction of travel of the microdroplets a region of the microfluidic space continuously varies or may be caused to continuously vary in depth.

Suitably the method described above is used with one of the tapering arrangements of the device described herein and in one embodiment the microdroplets undergo progressive compression as they translocate through the tapering space. This enables the maximum translocation speed of the microdroplets to be varied. The method is especially applicable to the sequencing method we have described in our earlier patents referred to herein in which a nucleic acid analyte is progressively pyrophosphorolysed into its constituent single nucleoside triphosphates which are subsequently captured by various oligonucleotide probe systems to generate used probe molecules which can be caused to emit nucleotide-characteristic fluorescence after undergoing endonucleolysis and/or exonucleolysis. In one embodiment of this method, which is particularly applicable to the device of the present invention, a stream of microdroplets comprised of an aqueous pyrophosphorolysing medium dispersed in an immiscible carrier phase such as a mineral or silicone oil is translocated by optoelectrowetting forces towards a region at or near the apex of the taper where they are caused to traverse one by-one a nucleic acid analyte attached to particle such as a microbead. In doing so, the analyte is progressively pyrophosphorolysed into its constituent single nucleoside triphosphate molecules which are captured by each microdroplet in the stream prior to the microdroplet becoming detached from the particle. Suitably, in the zone in which the microdroplets traverse the particle they undergo compression; for example, by depth-profiling of the wall(s) of the device.

Thereafter, the detached microdroplets are caused to translocate away from the particle and the apex via the same or another optoelectrowetting pathway. These detached microdroplets can then be caused to merge with secondary microdroplets containing fluorescent detector probes; for example but not limited to those of the type described in our earlier patent applications (see for example WO2014053853, WO2014167323, WO2016012789, EP16187112, EP16187493, EP161897791 and EP17171168 to which the reader is directed for further details) and the enzymes required to make the probes function (some or all of ligase, polymerase, exonuclease, endonuclease etc.). These latter detector probes are characterised by being quenched in their unused state but after use are capable of undergoing exonucleolysis and/or endonucleolysis to release their constituent reporter fluorophores in a fluorescing state.

Following such microdroplet merging and a period of thermal cycling and/or incubation to allow the detection reaction to occur, the microdroplets may be individually interrogated by a light source/photodetector arrangement to stimulate and detect any fluorescence arising from the free fluorophores. Thereafter the signal generated by the photodetector can be processed by a microprocessor and sequencing algorithms. By this means, the device and the method can be used to sequence DNA or RNA of either synthetic or natural origin.

The method described above is also suitable for screening for immune cell functionality. In one embodiment of this method, a set of microdroplets comprised of an aqueous medium, containing immune cells, dispersed in an immiscible carrier phase such as a mineral, silicone or fluorocarbon oil is translocated by optoelectrowetting forces towards a region at or near the apex of the taper where they are caused to traverse, one by one, a set of particles such as a microbeads which are decorated with antigen(s) relevant to the expected protein expression(s) of the immune cells. In doing so the excreted proteins from the immune cells, such as antibodies, are allowed to interact with the decorated beads creating non-competitive immunoassay sandwich constructs with another antigen or enzyme corresponding to the excreted protein and labelled with a suitable signal reporter such as a fluorescent dye. Thereafter, the immune cell containing microdroplets are caused to translocate away from the particles and the apex, along the same or other optoelectrowetting pathways. The particles at or near the apex are then suitably subjected to subsequent and repeating merge and split operations, for example with a second set of aqueous cell-free microdroplets to lower the concentration of unquenched unbound signal labelled antigen or enzyme molecules.

Following these 'wash' steps the particles may be individually interrogated using a light source/photodetector to probe the signal, for example fluorescence, arising from the immunoassay sandwich construct. By these means, the device and the method can be used to determine the protein expression from a specific set of cells and separate these cells from cells which do not excrete the particular protein(s) in questions.

The protein excreting cells can further be subjected to other reporting systems, for example immunoassays or FRET reporters; lysed in order to form a library of genes expressed by the cells; or recovered off-chip and be subjected to genetic assays to determine the coding DNA responsible for the behaviour seen on-chip.

The invention claimed is:

1. A microfluidic device for manipulating microdroplets simultaneously comprising (a) a microfluidic space defined at least in part by an arrangement of opposed first and second containing composite walls, wherein the first composite wall comprised of:
  a first substrate
  a first conductor layer on the substrate;
  a photoactive layer activated by electromagnetic radiation in the wavelength range 400-1000 nm on the conductor layer;
  a first dielectric layer on the photoactive layer;
a second composite wall comprised of:
  a second substrate;
  a second conductor layer on the substrate;
  optionally a second dielectric layer on the conductor layer;
an A/C source to provide a voltage across the first and second composite walls connecting the first and second conductor layers;
at least one source of electromagnetic radiation having an energy higher than the bandgap of the photoexcitable layer adapted to impinge on the photoactive layer to induce corresponding transient optoelectrowetting electrode locations on the surface of the first dielectric layer; and
a microprocessor for manipulating the points of impingement of the electromagnetic radiation on the photoactive layer so as to vary the disposition of the transient optoelectrowetting electrode locations thereby creating at least one electrowetting pathway along which the microdroplets may be caused to move; and
(b) disposed on or within at least one of the containing composite walls, transient optoelectrowetting electrode locations arranged in a pathway, wherein at least one direction substantially parallel to that of the pathway a region of the microfluidic spaces continuously varies or may be caused to continuously vary in depth by an applied force.

2. The microfluidic device of claim 1, wherein the region continuously tapers up or down along the pathway from or to a maximum dimension of less than 150% of the diameter of the microdroplets when measured in a non-compressed state.

3. The microfluidic device of claim 1, wherein at least one of the containing composite walls includes at least one inlet for introducing the microdroplets into the microfluidic space.

4. The microfluidic device of claim 1, wherein the optoelectrowetting electrode locations are arranged on or within the containing composite wall(s) to form at least one pathway which is at least in part orientated substantially parallel to the direction of taper along which the microdroplets translocate.

5. The microfluidic device of claim 1, further comprising multiple pathways arranged to intersect with each other so that the translocating microdroplets can be caused to merge with secondary microdroplets at one or more zones in the microfluidic region.

6. The microfluidic device of claim 2, further comprising at least one particle-receiving location towards the apex of the taper and capable of receiving a particle bearing an analyte sample to be traversed by microdroplets translocating in at least one of the pathways.

7. The microfluidic device of claim 1, further comprising at least one window in the containing composite wall(s) through which the microdroplets can be interrogated using a light source and a photodetector.

* * * * *